US006709610B2

(12) United States Patent
Van Buskirk et al.

(10) Patent No.: US 6,709,610 B2
(45) Date of Patent: *Mar. 23, 2004

(54) ISOTROPIC DRY CLEANING PROCESS FOR NOBLE METAL INTEGRATED CIRCUIT STRUCTURES

(75) Inventors: Peter C. Van Buskirk, Newtown, CT (US); Frank DiMeo, Jr., Danbury, CT (US); Peter S. Kirlin, Austin, TX (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 9 days.

This patent is subject to a terminal disclaimer.

(21) Appl. No.: 09/768,494

(22) Filed: Jan. 24, 2001

(65) Prior Publication Data

US 2002/0011463 A1 Jan. 31, 2002

Related U.S. Application Data

(63) Continuation of application No. 09/093,291, filed on Jun. 8, 1998, now Pat. No. 6,254,792, which is a continuation-in-part of application No. 08/966,797, filed on Nov. 10, 1997, now Pat. No. 6,018,065.

(51) Int. Cl.$^7$ .................................................. C23F 1/30
(52) U.S. Cl. .......................... 216/64; 216/67; 216/75; 134/1.2; 134/1.3; 252/79.1; 438/710; 438/720
(58) Field of Search .............................. 216/64, 65, 66, 216/67, 75; 134/1.2, 1.3; 252/79.1; 435/710, 720

(56) References Cited

U.S. PATENT DOCUMENTS

| | | | |
|---|---|---|---|
| 4,659,426 A | 4/1987 | Fuller et al. | |
| 5,492,855 A | * 2/1996 | Matsumoto et al. | 437/60 |
| 5,814,238 A | 9/1998 | Ashby et al. | |
| 5,854,104 A | * 12/1998 | Onishi et al. | 438/240 |
| 5,911,887 A | 6/1999 | Smith et al. | |
| 5,976,928 A | 11/1999 | Kirlin et al. | |
| 6,018,065 A | 1/2000 | Baum et al. | |
| 6,143,191 A | * 11/2000 | Baum et al. | 216/63 |
| 6,254,792 B1 | * 7/2001 | Van Buskirk et al. | 134/1.1 |
| 6,265,318 B1 | * 7/2001 | Hwang et al. | 438/720 |
| 6,368,518 B1 | * 4/2002 | Vaartstra | 216/67 |
| 2001/0024679 A1 | * 9/2001 | Baum et al. | 427/58 |

FOREIGN PATENT DOCUMENTS

| WO | WO 98/00859 | * 1/1998 | H01L/21/302 |
|---|---|---|---|

OTHER PUBLICATIONS

Tea et al., Journal of Microelectromechanical Systems, vol. 6, No. 4, pp. 363–372, Dec. 1997.*

(List continued on next page.)

*Primary Examiner*—Allan Olsen
(74) *Attorney, Agent, or Firm*—Margaret Chappuis; Steven J. Hultquist

(57) ABSTRACT

A method for removing from a microelectronic device structure a noble metal residue including at least one metal selected from the group consisting of platinum, palladium, iridium and rhodium, by contacting the microelectronic device structure with a cleaning gas including a reactive halide composition, e.g., $XeF_2$, $SF_6$, $SiF_4$, $Si_2F_6$ or $SiF_3$ and $SiF_2$ radicals. The method may be carried out in a batch-cleaning mode, in which fresh charges of cleaning gas are successively introduced to a chamber containing the residue-bearing microelectronic device structure. Each charge is purged from the chamber after reaction with the residue, and the charging/purging is continued until the residue has been at least partially removed to a desired extent. Alternatively, the cleaning gas may be continuously flowed through the chamber containing the microelectronic device structure, until the noble metal residue has been sufficiently removed.

17 Claims, 3 Drawing Sheets

OTHER PUBLICATIONS

Koteki, D.E., "A Review of High Dielectric Materials for DRAM Capacitors", *Integ. Ferro.*, 1997, vol. 16, pp. 1–19.

Jeon, et al., "Thermal Stability of Ir/Polycrystalline–Si Structure for Bottom Electrode of Integrated Ferroelectric Capacitors", *Appl. Physics Lett.*, 1997, vol. 71(4), pp. 467–469.

Williams, et al., "Etch Rates for Micromachining Processing", *Journ. For Microelectromechanical Systems*, Dec. 1996, vol. 5 (4), pp. 256–269.

Vugts, et al., "Si/XeF$_2$ Etching–Temperature Dependence", 1996, *J. Vac. Sci. Tech. A.* vol. 14(5), pp. 2766–2774.

P.C. Fazan, et al., "Stacked Capacitor Modules for 64 Mb DRAMs and Beyond", *Semiconductor Inter.*, 1992, vol. 108, pp. 108–112.

L. H. Parker, et al., Ferroelectric Materials for 64Mb and 256Mb DRAMs, *IEEE Circuits and Devices Mag.*, Jan. 1990, pp. 17–26.

R. E. Sievers, et al., "Volatile Barium B–Diketonates for Use as MOCVD Precursors", *Coord. Chem. Rev.*, 1993, pp. 285–291.

C. Farrell, et al., "A Reactive Ion Etch Study for Producing Patterned Platinum Structures", Presented at ISIF 96, Mar. 18,19,20, 1996 Tempe AZ. (to be published in Integrated Ferroelectrics).

K. R. Milkove and C. X. Wang, "Insight into the dry cleaning of Fence Patterned Platinum Structures", *J. Vac. Sci. Tech. A*, 1997, vol. 15(3), pp. 596–603.

Chang, F.I., et al., "Gas Phase Silicon Micromachining with Xenon Difluoride", *Proc of SPIE*, 1995, vol. 2641, pp. 117–128.

Bensaola, A. et al., "Low Temperature Ion Beam Enhanced Etching of Tungsten Films with Xenon Difluroide", *Appl. Phys. Lett.*, Dec. 1986, vol. 49(24), pp. 1663–1664.

G. Stauf, "BaSrTiO3 Etching for Advanced Microelectronic Devices", U.S. Army Missile Command, Report No., DAAH01–96–C–R035, Jan. 10, 1996–Jan. 30, 1998.

Ebsworth, E.A.V., et al., "Formation of Iridium Fluoroacyl Complexes by Reaction of Iridium Carbonyls with Xenon Difluoride and Reactions of these to Generate Unusual Acyl Complexes", *J. Chem. Soc., Dalton Trans.*, 1993, ISS. 7, pp. 1031–1037.

Blake, A.J., et al., "Novel Reaction of an Iridium Carbonyl Complex with Xenon Difluoride: The First Metal Fluoroacyl Complex", *J. Chem. Soc.*, Chem. Commun.,1988, ISS.8, pp. 529–530.

Sladkey, F.O., et al., "Xenon Difluoride as a Fluoride Ion Donor" *J. Chem. Soc. A*, 1969, vol. 14, pp. 2179–2188.

* cited by examiner

US 6,709,610 B2

ISOTROPIC DRY CLEANING PROCESS FOR NOBLE METAL INTEGRATED CIRCUIT STRUCTURES

RELATED APPLICATIONS TO WHICH PRIORITY IS CLAIMED

This is a continuation of U.S. application Ser. No. 09/093,291 filed Jun. 8, 1998, and issued Jul. 3, 2001 as U.S. Pat. No. 6,254,792, which in turn is a continuation-in-part of U.S. application Ser. No. 08/966,797 filed Nov. 10, 1997, and issued Jan. 25, 2000 as U.S. Pat. No. 6,018,065.

GOVERNMENT RIGHTS IN INVENTION

Some aspects of this invention were made in the performance of U.S. Government Contract No. DAA HOI 96-C-RD35, "$BaSrTiO_3$ Etching for Advanced Microelectronic Devices." The U.S. Government has certain rights in the invention hereof.

BACKGROUND OF THE INVENTION

1. Field of the Invention

The present invention relates to an isotropic dry cleaning process for noble metal integrated circuit structures.

2. Description of the Related Art

Thin films of noble metals (Pt, Pd, Ir, Rh) have become technologically important in integrated circuits (ICs) as electrodes for ferroelectric and high ε thin films in FeRAMs, DRAMs, RF and microwave MMICs, pyroelectric IR focal plane detector arrays, etc.

The absence of viable dry etching techniques for submicron patterning of these electrodes is a chronic problem that has threatened to retard or even prevent widespread use of these materials. The present dry-etching approaches utilize plasmas for reactive ion etching (RIE), are chlorine-based, and result in significant residue being left on the microelectronic device structure after the etch process has been completed.

Depending on the type of structure that is being formed by the patterning step, this post-etch residue may result in short circuiting, undesired topography or other deficiencies in the operation of the circuit element in subsequent use of the product microelectronic device. Prevention of the formation of such residues may be achieved in some instances by manipulating the reactive ion etching (RIE) process parameters, but such process manipulation results in undesirable sidewall slopes in the microelectronic device structure that effectively prevent useful submicron capacitors from being fabricated.

Alternatively, the residue resulting from RIE can be removed by wet rinsing techniques, after the etch process has been completed. Wet rinsing techniques are however generally unsatisfactory, because a significant fraction of the residue may be transported in suspension in the rinse media, allowing a small fraction of the residue solids to redeposit on the wafer, and thereby reducing device yield.

Further, in some microelectronic device structure geometries, the residue may not be removed using wet rinsing methods.

Another drawback of wet rinsing methods is the need for a separate process tool to implement the wet rinsing clean-up, which adds to the capital equipment and operating costs of the process system.

It would therefore be a significant advance in the art of integrated circuit device fabrication, in which noble metal films are formed on the device substrate as electrodes or other structural components of the device, to provide an effective cleaning process for removing unwanted residues on the integrated circuit structure after etching or other process fabrication steps.

SUMMARY OF THE INVENTION

The present invention relates to a method for removing noble metal residue from a microelectronic device structure during the fabrication thereof, by contacting the microelectronic device structure with a gas-phase reactive halide composition, e.g., $XeF_2$, $SF_6$, $Si_2F_6$, $SiF_4$, or $SiF_2$ and/or $SiF_3$ radicals, for sufficient time and under sufficient conditions to at least partially remove the noble metal residue.

Such "dry clean" method of the invention effects an isotropic dry etching of the noble metal residue for removal thereof. The isotropic dry etching is carried out under low-pressure exposure of the noble metal residue to the reactive halide gas.

The reactive halide may comprise any suitable halide substituent, e.g., fluorine, bromine, chlorine, or iodine, with fluorine generally being most preferred. The reactive halide agent may itself comprise the reaction product of an initial reaction, such as the reaction of $XeF_2$ with silicon to form $SiF_2$ and/or $SiF_3$ radicals as the reactive halide agent. In this manner $SF_6$, $SiF_4$ or $Si_2F_6$ may be used with an activation source (ion beam, electron beam, ultra violet or laser) to produce the reactive radical species.

The invention contemplates two main cleaning techniques for using the reactive halide gas as an isotropic noble metal etch agent to remove residual noble metal deposits from the microelectronic device structure.

The first technique is a batch contacting method wherein a chamber containing the microelectronic device structure is evacuated and backfilled with the reactive halide gas or a mixture of the reactive halide gas and other gas(es), either inert or reactive. After the reactive halide is allowed to react for a predetermined amount of time, the chamber is evacuated and backfilled again with fresh cleaning gas. The evacuation pressure can be less than or equal to 50 mTorr. The backfill pressure can be from about 50 mTorr to about 2 Torr, the exposure time can be from about 10 seconds to about 10 min, and the number of exposure cycles is not limited, but will depend on the amount of material to be removed.

The second technique using the reactive halide gas as an isotropic etch agent is a continuous gas flow method. In this technique, a steady state flow of the reactive halide gas, e.g., $XeF_2$, $SF_6$, $Si_2F_6$ or $SiF_4$, is introduced to the chamber containing the microelectronic device structure to be cleaned. Either pure reactive halide gas or a mixture of the reactive halide and other gas(es), either inert or reactive, may be used. The partial pressure of the reactive halide gas can be from about 50 mTorr to about 2 Torr and total flow rate of the reactive halide gas can be from about 1 standard cubic centimeter per minute (sccm) to about 10 standard liters per minute (slm).

In either case of batch or continuous operation, the microelectronic device structure to be cleaned may be held at temperatures in the range of from about −50° C. to about 200° C.

In the foregoing methodology, the reactive halide gas may for example comprise a $XeF_2$ vapor. Such vapor may be obtained from the sublimation of $XeF_2$ solid crystals. $XeF_2$ will sublime at room temperature, but may be heated to increase the rate of sublimation.

Additionally, the $XeF_2$ may first be reacted with elemental silicon, and the resultant reaction product used as the etching gas. It is known that $XeF_2$ etches silicon to produce $SiF_4$, $Si_2F_6$ and $SiF_2$ and $SiF_3$ radicals.

The reactive halide composition may also be produced in an upstream plasma, e.g., $SiF_2$ and $SiF_3$ radicals may be formed by passing $SiF_4$ gas through a remote plasma.

The method of the invention is usefully employed for removal of noble metal residues comprising Ir, Rh, Pd and/or Pt, and may be utilized for cleaning hybrid electrodes comprising alloys or combinations of such metals, as well as alloys or combinations of one or more of such metals with other (non-noble) metals.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
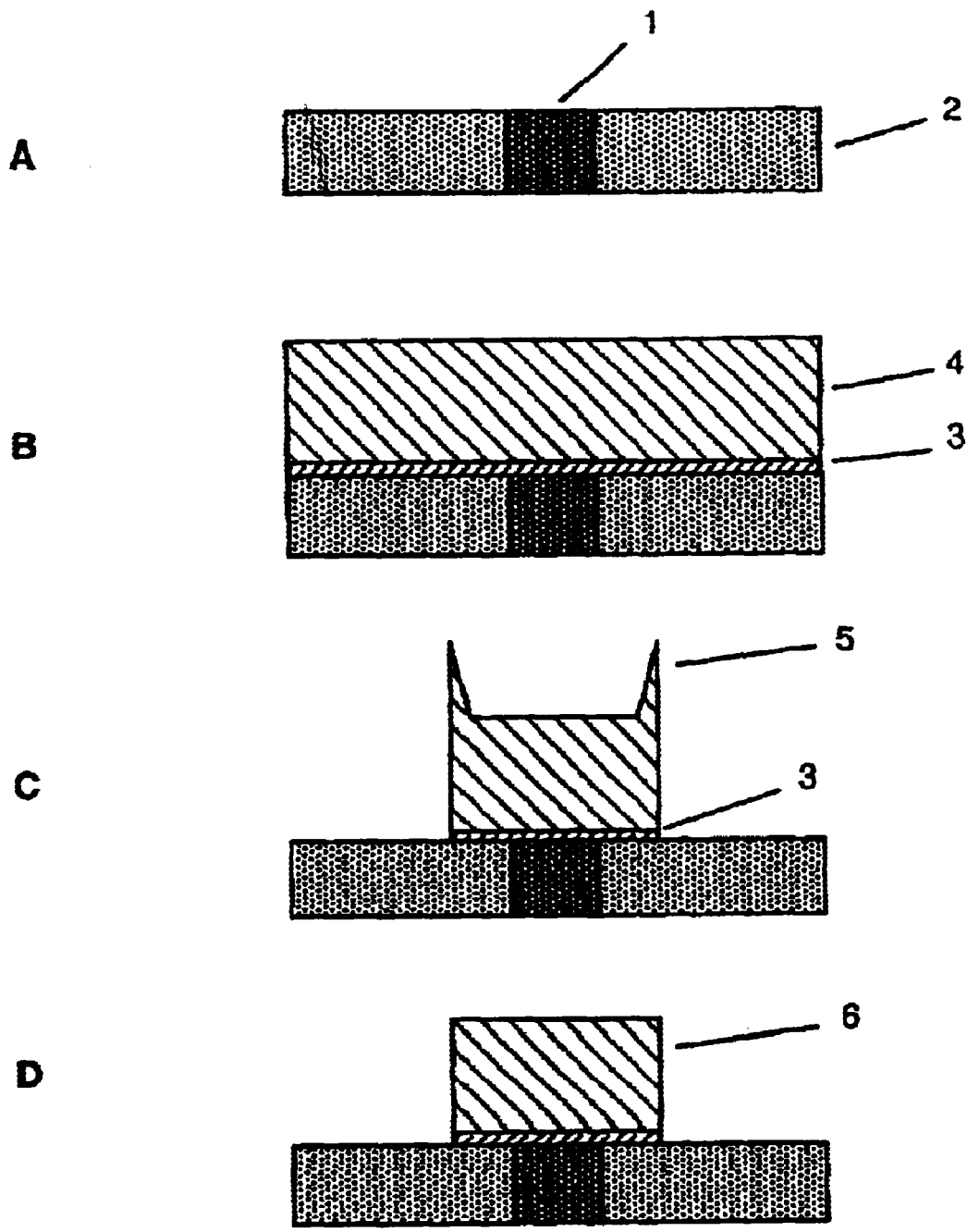
FIG. 1 is a process flow of a fabrication sequence embodying the method of the present invention, in one aspect thereof.

The disclosure of U.S. patent application Ser. No. 08/966, 796 filed Nov. 10, 1997 in the names of Thomas H. Baum and Frank DiMeo, Jr. for "METHOD FOR ETCH FABRICATION OF IRIDIUM-BASED ELECTRODE STRUCTURES," is incorporated herein by reference in its entirety.

In accordance with the method of the present invention, noble metal residue is removed from a microelectronic device structure including same, by contacting the microelectronic device structure with a gas-phase reactive halide composition, e.g., $XeF_2$, $SF_6$, $SiF_4$, $Si_2F_6$, or $SiF_3$ and/or $SiF_2$ radicals for sufficient time and under sufficient conditions to at least partially remove the noble metal residue.

The method of the invention may be advantageously used to remove residue from a microelectronic device structure, subsequent to reactive ion etching of noble metal electrode films thereon, for patterning of the electrode in the fabrication of the microelectronic device, and/or following chemical mechanical polishing (CMP) of the electrode or a precursor structure therefor.

As used herein, the term "microelectronic device structure" refers to a microelectronic device or a processing step towards the formation of a structure for the microelectronic device that must be subjected to subsequent processing or treatment steps in order to fabricate the final product device.

The method of the present invention obviates the deficiencies of the prior art wet rinsing techniques that have been used to remove residues when noble metal structures are formed on the surface of a microelectronic substrate, device or precursor article.

The isotropic dry etch method of the present invention may be practiced with reactive halogenated compounds such as $XeF_2$ and/or other halide compositions as agents for removing extraneous noble metal residues that are present on the microelectronic device structure subsequent to forming noble metal electrodes or other integrated circuit components thereon, and reactive ion etching (RIE) and/or chemical mechanical polishing (CMP) thereof. Alternatively, the removal agent for the noble metal residue may comprise a halogenated radical species such as $SiF_2$ or $SiF_3$ radicals, formed by prior reaction as hereinafter more fully disclosed.

As used herein, the term "noble metal" means a metal of the platinum group, viz., platinum, palladium, iridium or rhodium, as well as alloys and combinations including one or more of such metals, e.g., with other non-noble metal(s).

The invention contemplates two main cleaning techniques for using the reactive halide gas as an isotropic noble metal etch agent to remove residual noble metal deposits from the microelectronic device structure.

The first technique is a batch contacting method wherein a chamber containing the microelectronic device structure is evacuated and backfilled with the reactive halide gas or a mixture of the reactive halide gas and other gas(es), either inert or reactive. After the reactive halide is allowed to react for a predetermined amount of time, the chamber is evacuated and backfilled again with fresh cleaning gas. The evacuation pressure can be less than or equal to 50 mTorr. The backfill pressure can be from about 50 mTorr to about 2 Torr, the exposure time can be from about 10 seconds to about 10 min, and the number of exposure cycles is not limited, but will depend on the amount of material to be removed.

The second technique using the reactive halide gas as an isotropic etch agent is a continuous gas flow method. In this technique, a steady state flow of the reactive halide gas, e.g., $XeF_2$, $SF_6$, $Si_2F_6$ or $SiF_4$, is introduced to the chamber containing the microelectronic device structure to be cleaned. Either pure reactive halide gas or a mixture of the reactive halide and other gas(es), either inert or reactive, may be used. The partial pressure of the reactive halide gas can be from about 50 mTorr to about 2 Torr and total flow rate of the reactive halide gas can be from about 1 standard cubic centimeter per minute (sccm) to about 10 standard liters per minute (slm).

In either case of batch or continuous operation, the microelectronic device structure to be cleaned may be held at temperatures in the range of from about −50° C. to about 200° C.

The dry clean process of the present invention may be carried out at any suitable process condition, including ambient temperature, low temperature and elevated temperature regimes, as well as varying pressure regimes. For example, the cleaning process may be carried out at room temperature conditions involving the sublimation of $XeF_2$ to generate an active cleaning agent. $XeF_2$ may also be first reacted with another compound, such as silicon, to generate an active cleaning agent comprising $SiF_2$ or $SiF_3$ radicals.

The time and contacting conditions for the reactive halide etch process may be readily determined by those of ordinary skill in the art. The nature and extent of the etching of the deposited noble metal-based material may be empirically determined while varying the time and/or contacting conditions (such as temperature, pressure, concentration and partial pressure) of the etching agent to identify the process conditions producing a desired etching result.

In the dry clean of the noble metal residue to etchingly remove same from the microelectronic device structure, the etch rates of the cleaning agent can optionally be enhanced through the use of Lewis-based adducts or electron back-bonding species, e.g., carbon monoxide, trifluorophosphine, trialkylphosphines, etc. These cleaning enhancement agents accelerate the rate of etching by enhancing the volatility of the etch by-products and noble metal $(halide)_x$ species or noble metal $(halide\ radical)_x$ species.

For example, in the case of iridium and/or iridium oxide as the noble metal on the substrate, the step of contacting the iridium-based material with a cleaning gas including the xenon halide etching reagent may be carried out with a cleaning enhancement agent such as carbon monoxide to assist in the volatilization and removal of $Ir(X)_{1-6}$ (where X=halide) species from the iridium-based material on the substrate. Where X=chlorine, bromine, fluorine or iodine in the presence of CO serves to enhance the reactant volatility through the formation of $(CO)_y Ir(X)_{1-6}$. These enhancement agents can be used advantageously for etching Ir in halogen-based plasmas, ion beams and in hybrid etching schemes. Corresponding use of CO or other platinum metal hexafluorides may be utilized to remove other platinum metal residues on semiconductor device structures.

In another example, in the case of iridium and/or iridium oxide as the noble metal on the substrate, the step of contacting the iridium-based material with a cleaning gas including the xenon halide etching reagent may be carried out with a co-etchant such as $SF_6$, $Si_2F_6$, $SiF_4$ or radical species such as $SiF_3$ and $SiF_2$ to assist in the volatilization and removal of $Ir(X)_{1-6}$ (where X=silicon halide complex) species from the iridium-based material on the substrate.

The etching process using the xenon halide etching agent may also be enhanced by use of inert gases. In general, ion beam-assisted, plasma-assisted or photo-assisted techniques may be employed to enhance the etching removal of the noble metal residue, as for example by decreasing the time required for removal, or increasing the extent of removal in a given time, etc.

In application to the fabrication of specific types of microelectronic device structures, the invention has illustrative utility in the fabrication of capacitor structures. There are three principal types of capacitor geometries and associated processing paths, hereafter referred to as Type 1, Type 2 and Type 3, in which the method of the present invention offers a significant economic or enabling advantage over the methods of the prior art.

Capacitor arrays in high-density memories (>64 Mb) are typically made by patterning the bottom electrode prior to deposition and patterning of the dielectric and top electrode layers. This is referred to as a Type 1 structure.

For Type 1 structures, the prior art has used a combination of mechanical liquid agitation and partial dissolution of the residue to "clean up" the noble metal residues.

The process of the present invention provides an effective alternative to such prior art wet methods for removing noble metal residues from RIE-patterned bottom electrodes.

The process of the invention is also usefully applied to patterning approaches that define the entire capacitor in one step, including RIE of the entire metal-dielectric stack (Type 2) and chemical mechanical planarization, or chemical mechanical polishing, as such operation is sometimes termed (Type 3).

In chemical mechanical planarization, capacitors are formed in recesses and excess protruding dielectric and metal is removed by polishing, as more fully described in copending U.S. application Ser. No. 08/975,366 filed Nov. 20, 1997 in the names of Peter C. Van Buskirk and Peter S. Kirlin for "CHEMICAL MECHANICAL POLISHING OF FeFRAM CAPACITORS," the disclosure of which hereby is incorporated herein by reference in its entirety.

Type 1 Capacitor Structures

As mentioned, this structure is used for very high-density memories, such as those with memory density >64 Mb. Parts of the capacitor are formed on the sidewalls, with potential large increases in capacitor area.

Referring to FIG. 1A of the drawings, a Type 1 capacitor array is formed over an array of transistors (not shown), which are contacted preferably by conductive plugs 1. The conductive plugs are planarized on the surface of the isolation dielectric 2, or subsequent to capacitor formation by etching vias in which conductive plugs are formed, as shown in FIG. 1A.

Next, as shown in FIG. 1B, the barrier layer 3 and bottom electrode 4 are deposited, using conventional methods such as CVD or sputtering. The bottom electrode is then patterned using RIE or a similar metal etch, as illustrated in FIG. 1C, prior to capacitor dielectric (high $\epsilon$, ferroelectric, etc.) deposition.

When the electrode is patterned using the predominantly physical mechanism of the impinging ions, involatile material that is sputtered from between the electrodes is redeposited on the sidewalls of the photoresist (or hard mask), and when the mask is removed, the redeposited layers remain. These redeposited features 5, sometimes characterized as "ears," are surprisingly robust.

The dry etch cleaning method of the present invention is usefully applied in the fabrication of such Type 1 structure and may be advantageously implemented in-situ in the RIE reactor. As shown in FIG. 1D, the isotropic nature of the dry clean etch effectively removes the ears that were formed by the highly anisotropic RIE process.

The result is smooth bottom electrodes 6 that will increase device yield because of the absence of sharp features which would if otherwise present serve to enhance E-fields in the capacitor dielectric. Subsequent processing of the capacitor may then proceed (not shown), comprising dielectric deposition, dielectric patterning, top electrode deposition and patterning, and metallization post oxidizing bake step to complete the formation of the integrated circuit.

In this Type 1 application, the process of the present invention provides a significant economic advantage over prior art wet methods. As mentioned, prior art wet methods, although effective, result in significant decrease in device yield as well as decreased throughput.

Type 2 Capacitor Structures

Figure 2:
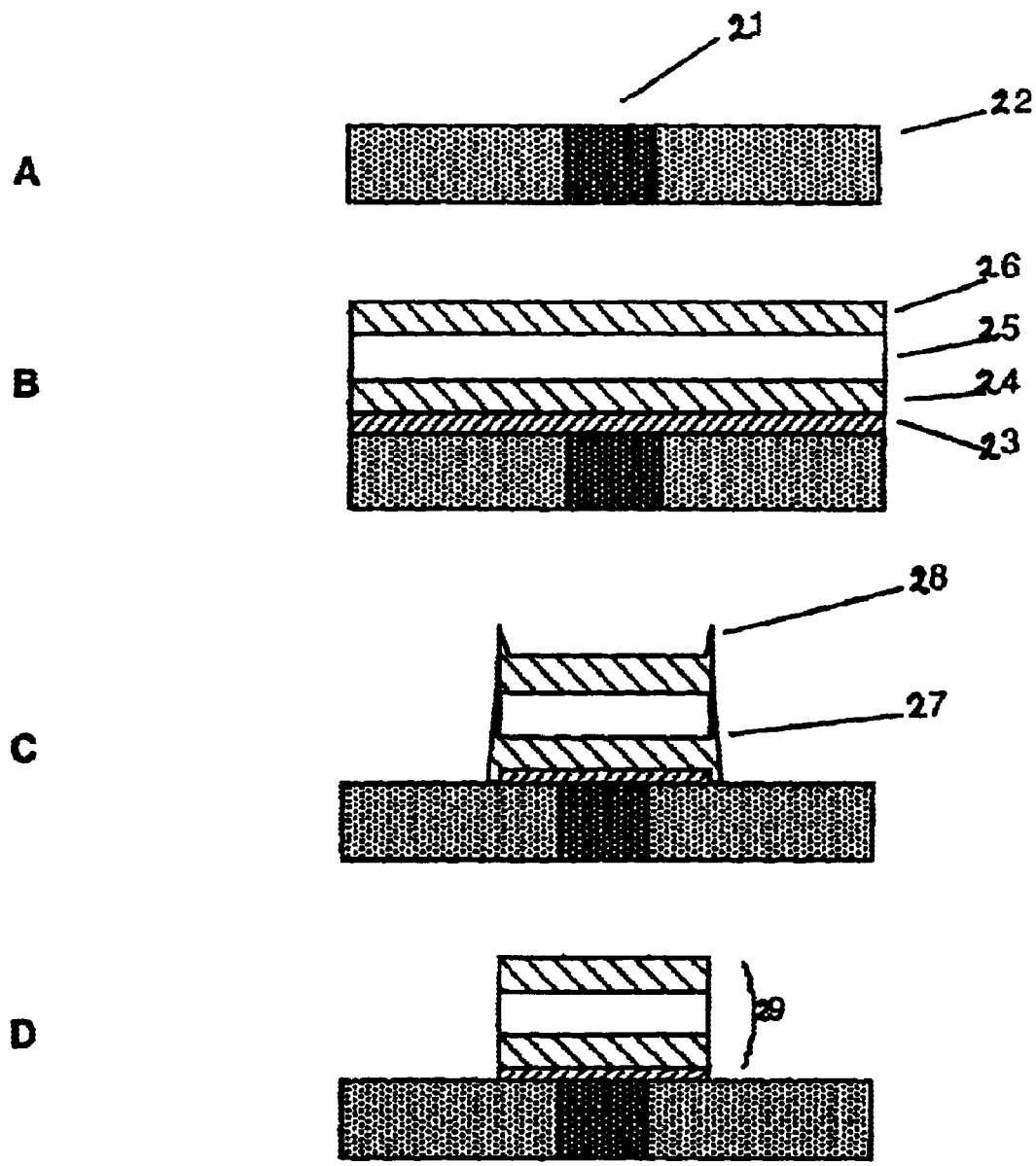
FIG. 2 is a schematic representation of a process flow of an alternative method embodiment of the invention.

This type of structure is illustrated in FIG. 2 and is usefully employed in lower density memory arrays (<64 Mb), where the area of the capacitor allows sufficiently high capacitance or remanent polarization.

In the process flow of FIG. 2, the capacitor array is formed on a planar surface of an isolation dielectric 22, over an array of transistors (not shown). The transistors in this structure are contacted by conductive plugs 21 that have been planarized using CMP or other planarization techniques that are well known in the art. The plug and dielectric structure is illustrated in FIG. 2A.

In this fabrication method, the entire capacitor system of layers, including conductive barrier 23, bottom electrode 24, dielectric (high $\epsilon$, ferroelectric, etc.) material 25 and top electrode 26 are deposited sequentially, to produce the structure shown in FIG. 2B.

The capacitors are next defined using conventional microlithography and anisotropic dry etching processes, using either 2 mask levels or 1 mask level. The use of 1 mask level is the preferred embodiment to produce the structure of FIG. 2C, and is currently the most widespread technique for fabricating FeRAM capacitors.

The comparative advantages of a 2 mask process are well known, and include reducing the tendency for increased leakage currents that occur when a 1 mask approach is used. A 2 mask approach patterns the top electrode (TE) and bottom electrode (BE) to different areas (the TE is smaller), thereby reducing the chance for short circuits at the electrode edge. The 2-mask approach nonetheless is less economical than the 1 mask approach.

The method of the present invention permits the 1 mask approach to be utilized advantageously without the high level of leakage susceptibility that has been characteristic of prior art products made by such mask approach.

Due to the predominantly physical nature of the reactive ion etching process, residue collects on the sides of the capacitor structure 27, making short circuiting more likely. Additionally, sharp features ("ears") may also be present on the top edges of the top electrode 28, for the same reason as discussed hereinabove in connection with the fabrication of the Type 1 structure.

The process of the present invention is employed to remove the sidewall residue and the "ears". This process step in FIG. 2D removes metallic conductive residue from the edges of the capacitor, analogous to the use of the dry cleaning method of the invention in the fabrication of the Type 1 structure as described hereinabove.

In addition to the isotropic dry clean process, a post oxidizing bake may be performed, similar to that described above for the fabrication of the Type 1 structure. The result is a capacitor structure 29 that is formed with high yield in terms of short circuiting. In addition, the capacitor structure 29 does not have protrusions from the top edges of the top electrode. Such protrusions when present complicate the subsequent isolation of the capacitor array that is required before metallization can be carried out to complete the memory circuits of the structure.

The method of the present invention is of an enabling character in application to the fabrication of the Type 2 structure, since prior art wet methods do not effectively clean nominally planar surfaces with embedded metallic contamination.

Type 3 Capacitor Structures

Figure 3:
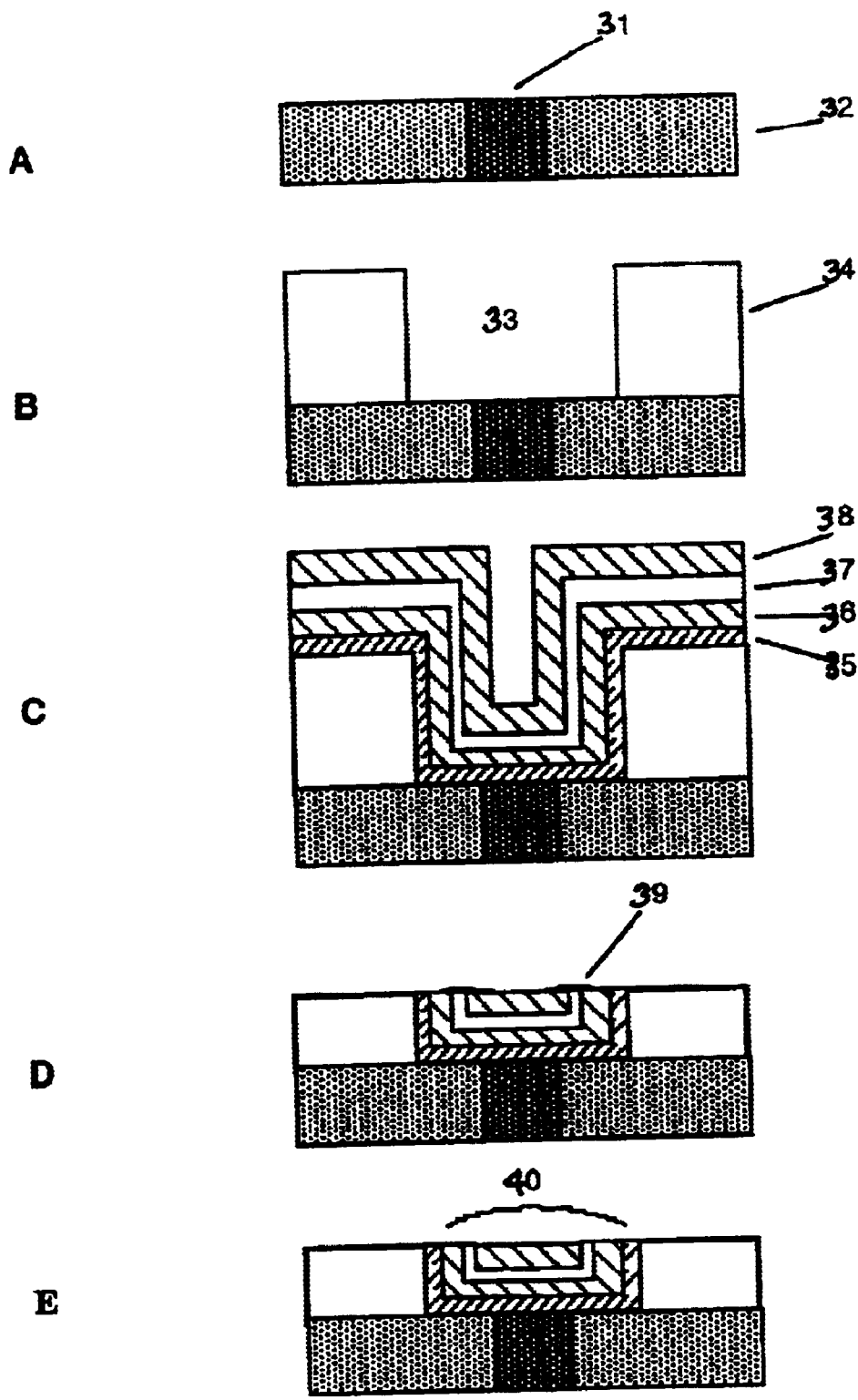
FIG. 3 is a schematic representation of a process flow for yet another method embodiment of the present invention.

This fabrication technique is shown in the process flow schematically illustrated in FIG. 3. Such fabrication technique may be utilized to completely avoid the need for RIE processes to pattern noble metals and complex oxide thin films, e.g., those comprising $PbZrTiO_3$, $SrBiTiO_3$ and $BaSrTiO_3$.

The FIG. 3 fabrication technique can be used to fabricate either high or low-density capacitor arrays, since enhanced capacitor area can be obtained from the sidewall contribution, if the aspect ratio of the recesses (depth/width) is large enough.

Such technique can also be used to fabricate low-density memory arrays, due to the inherent economic advantages of this methodology in minimizing the patterning complexity and the number of steps.

The capacitor array in the FIG. 3 fabrication method is formed on a planar surface of an isolation dielectric 32, over an array of transistors (not shown), which are contacted by the conductive plugs 31 illustrated in FIG. 3A. In this fabrication technique, capacitor recesses 33 are formed in a conventional dielectric material 34 ($SiO_2$ or $Si_3N_4$, for example).

The capacitor recesses are aligned over the conductive plugs 31, as shown in FIG. 3B. The capacitor recesses 33 will correspond to self-aligned capacitors over such conductive plugs once the patterning of the capacitors is completed.

The entire capacitor system of layers is then deposited sequentially to form the structure shown in FIG. 3C. The respective layers include conductive barrier 35, bottom electrode 36, dielectric (high $\epsilon$, ferroelectric, etc.) material 37, and top electrode 38.

The individual capacitors are next defined by chemical mechanical polishing (CMP) of the entire layer system to yield the structure shown in FIG. 3D. Once the structure is formed by CMP there may be significant metal contamination 39 along the edges of the capacitor on the top surface (which has been planarized) that will result in short circuiting of the capacitor if not removed from the structure. Such metallic contamination is typically due to incomplete removal and smearing of noble metal electrode material during the chemical mechanical polishing operation.

The process of the present invention next is utilized to remove the conductive metallic residue, to produce the structure as shown in FIG. 3E, and thereby allow the capacitors to function as intended.

In addition to the isotropic dry clean process, a post oxidizing bake may be employed to heal surface and/or subsurface damage to the dielectric (high $\epsilon$, ferroelectric, etc.) material. Such damage may be either chemical or physical in nature. The post oxidizing bake thereby imparts optimum insulating or ferroelectric properties (depending on the material of construction) to the dielectric material.

The result is a capacitor structure 40 shown in FIG. 3E that is formed with high yield (in terms of non-short circuiting device elements), in a highly economical manner. In this application (the fabrication of Type 3 structures), the process of the present invention is enabling in character, since wet cleaning methods of the prior art do not work well to clean planar surfaces with embedded metallic contamination.

Accordingly, while the invention has been described herein with reference to specific features, aspects and embodiments, it will be recognized that the invention may be widely varied, and that numerous other variations, modifications and other embodiments will readily suggest themselves to those of ordinary skill in the art. Accordingly, the ensuing claims are to be broadly construed, as encompassing all such other variations, modifications and other embodiments, within their spirit and scope.

What is claimed is:

1. A method for removing from a microelectronic device structure a noble metal residue including at least one metal selected from the group consisting of platinum, palladium, iridium and rhodium, the method comprising contacting the microelectronic device structure with a dry etching composition consisting essentially of (i) at least one dry etching agent selected from the group consisting of $XeF_2$, $SiF_4$, $Si_2F_6$, $SiF_2$ radicals, and $SiF_3$ radicals, and (ii) optionally, carbon monoxide.

2. The method according to claim 1, wherein the dry etching composition consists essentially of $XeF_2$.

3. The method according to claim 1, wherein the dry etching composition consists essentially of at least one dry etching agent selected from the group consisting of $SiF_4$, and $Si_2F_6$.

4. The method according to claim 1, wherein the dry etching composition consists essentially of at least one dry etching agent selected from the group consisting of $SiF_2$ and $SiF_3$ radicals.

5. The method according to claim 1, wherein the dry etching composition consists essentially of $SiF_2$ and $SiF_3$ radicals and the dry etching composition is generated by reaction of $XeF_2$ with silicon.

6. The method according to claim 1, wherein the dry etching composition consists essentially of $SiF_2$ and $SiF_3$ radicals and the dry etching composition is generated by passing $SiF_4$ through an energetic dissociation source.

7. The method according to claim 6, wherein the energetic dissociation source is selected from the group consisting of a plasma source, an ion source, an ultra violet source and a laser source.

8. The method according to claim 1, wherein said noble metal residue includes at least one metal selected from the group consisting of palladium, iridium and rhodium.

9. The method according to claim 1, wherein said dry etching composition consists essentially of (i) said at least one dry etching agent and (ii) carbon monoxide.

10. A method for removing from a microelectronic device structure a noble metal residue, the method comprising contacting the microelectronic device structure with a dry etching agent consisting essentially of (i) a gas-phase reactive halide composition and (ii) optionally, an agent for enhancing volatility of metal fluoride species formed by said contacting of the microelectronic device structure with the gas-phase reactive halide composition (i), to remove the residue, wherein the noble metal residue comprises iridium, and the gas-phase reactive halide composition comprises $XeF_2$ and at least one halide species selected from the group consisting of $SF_6$, $SiF_4$, $Si_2F_6$, $SiF_2$ radicals and $SiF_3$ radicals, and wherein the microelectronic device structure is further contacted with a cleaning enhancement agent.

11. The method according to claim 10, wherein the cleaning enhancement agent is selected from the group consisting of Lewis-base and electron back-bonding species.

12. The method according to claim 10, wherein the cleaning enhancement agent is selected from the group consisting of carbon monoxide, trifluorophosphine, and trialkylphosphines.

13. The method according to claim 10 wherein the cleaning enhancement agent comprises an agent for enhancing volatility of iridium fluoride species formed by said contacting of the microelectronic device structure with the gas-phase reactive halide composition.

14. A method of etching iridium, comprising contacting said iridium with $XeF_2$.

15. A method for removing a noble metal residue from a microelectronic device structure, wherein said noble metal residue is selected from the group consisting of palladium, iridium and rhodium, said method comprising contacting the microelectronic device structure with a composition consisting essentially of: (1) $SF_6$ and optionally (2) carbon monoxide.

16. A method for removing a noble metal residue comprising iridium, from a microelectronic devise structure disposed in a chamber, the method comprising evacuating the chamber, filing the chamber with a cleaning gas comprising $XeF_2$ and one or more radicals selected from the group consisting of $SiF_2$ and $SiF_3$, and retaining the cleaning gas in the chamber to react with the residue, to effect the removal of the noble metal residue from the microelectronic device structure.

17. A method for removing from a microelectronic device structure, a noble metal residue comprising iridium said method comprising, contacting the microelectronic device structure with a gas-phase reactive halide composition comprising $XeF_2$ and at least one cleaning enhancement agent selected from the group consisting of carbon monoxide, trifluorophosphine, and trialkylphosphines, to form at least one iridium halide species.

\* \* \* \* \*

UNITED STATES PATENT AND TRADEMARK OFFICE
CERTIFICATE OF CORRECTION

PATENT NO. : 6,709,610 B2
APPLICATION NO. : 09/768494
DATED : March 23, 2004
INVENTOR(S) : Peter C. Van Buskirk et al.

It is certified that error appears in the above-identified patent and that said Letters Patent is hereby corrected as shown below:

Column 1, line 16: "mance of U.S. Government Contract No. DAA HOI 96-C-" should be -- mance of U.S. Government Contract No. DAAH01-96-C- --.

Column 1, line 17: "RD35, "BaSrTiO 3 Etching for Advanced Microelectronic" should be -- R035, "BaSrTiO 3 Etching for Advanced Microelectronic --.

Signed and Sealed this

Second Day of November, 2010

David J. Kappos
*Director of the United States Patent and Trademark Office*